United States Patent [19]

DiMatteo

[11] 4,043,329
[45] Aug. 23, 1977

[54] PROTECTIVE DEVICE
[75] Inventor: Frank J. DiMatteo, Monroeville, Pa.
[73] Assignee: Caspel Industries, Bridgeville, Pa.; a part interest
[21] Appl. No.: 696,740
[22] Filed: June 16, 1976
[51] Int. Cl.$^2$ .............................................. A61F 13/00
[52] U.S. Cl. ................................................ 128/132 R
[58] Field of Search .................. 128/132 R, 161, 162; 2/2 R, 401–404

[56] References Cited
U.S. PATENT DOCUMENTS

| | | | |
|---|---|---|---|
| 2,534,934 | 12/1950 | Viniegra | 128/132 R |
| 3,176,686 | 4/1965 | Barnes | 128/132 R |
| 3,314,422 | 4/1967 | Phillips | 128/132 R |
| 3,339,208 | 9/1967 | Marbach | 128/132 R |
| 3,909,847 | 10/1975 | Holt et al. | 2/2 |

Primary Examiner—Lawrence W. Trapp
Attorney, Agent, or Firm—Robert D. Yeager; Robert DeMajistre

[57] ABSTRACT

A protective device is comprised of a rigid cup having sufficient volume to enclose the male genitals. A resilient padding is mounted on the edge of the cup and is adapted to contact the lower body. The resilient padding absorbs impact experienced by the cup. The resilient padding on the cup edge engages the body proximate to the superior ramii, the inferior ramii and the Ischial ramii of the pelvis with minimal contact with the interior upper thighs. The protective device so constructed causes impact experienced by the cup to be absorbed by the padding and the aforementioned portions of the pelvis.

6 Claims, 6 Drawing Figures

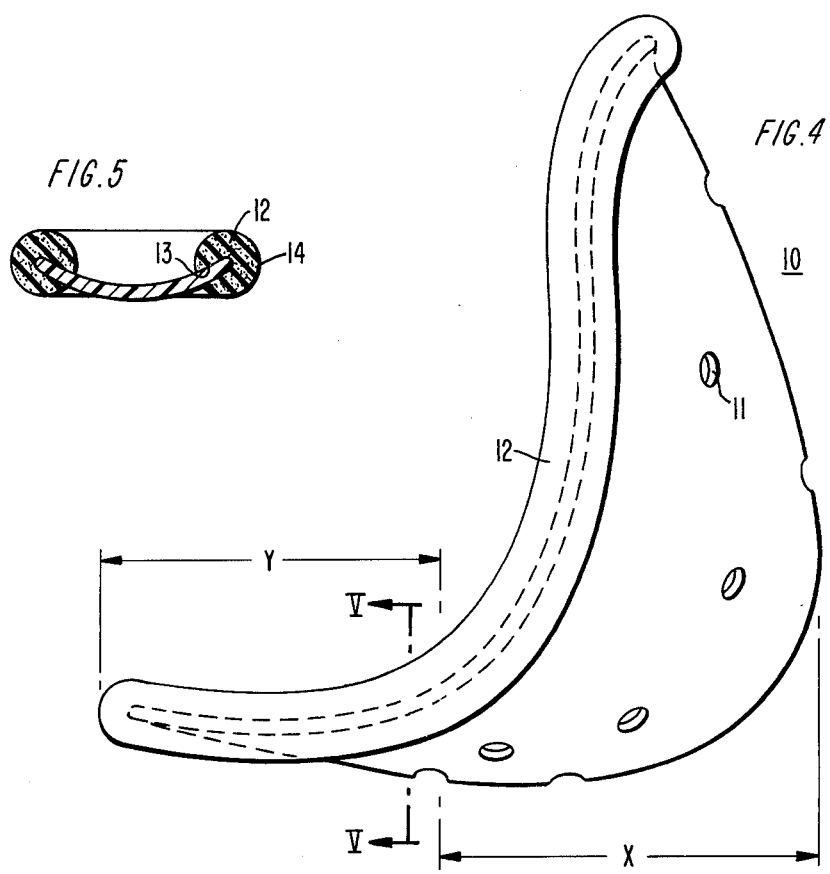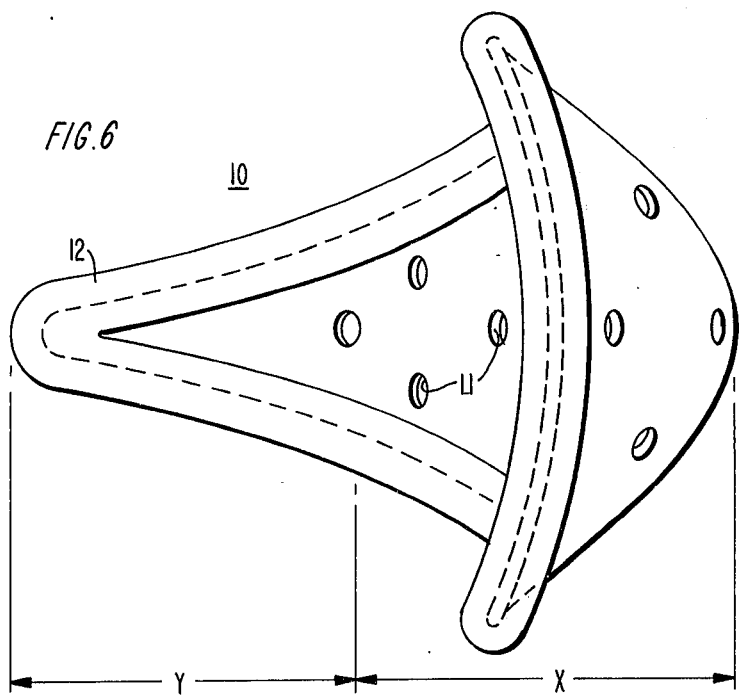

PROTECTIVE DEVICE

BACKGROUND OF THE INVENTION

1. Field of the Invention

This invention relates to protective devices and more particularly to protective devices for the male groin region.

2. Description of the Prior Art

Devices for protection of the male groin region are extensively utilized in athletics. Generally, these devices have been limited to the jockstrap used to support the male genitals and the "cup" which is a rigid plastic enclosure used to protect the genitals from impact.

In athletic competition particularly body contact sports such as football, hockey, rugby, soccer and the like a cup is worn by the competitors to avoid injury due to inadvertent blows to the groin area. Many of these inadvertent blows to the groin area direct force perpendicular to the axis of the body (i.e. the spine) and require the cup to absorb such blows. The cup effectively insulates the groin area and associated genitals from these perpendicular blows.

However, when the blow is directed upwardly and substantially parallel with the axis of the body, the protection of the genitals by the cup is hindered since the cup rides upwardly with the force of the blow and the edge of the cup tends to ride on the scrotum and impact the testes. Further, angular upward blows produce the same impediment to cup protection as the upward parallel blows.

Although the cup is somewhat effective in the contact sports hereinbefore described, special problems are encountered when the male groin area must be protected in the pursuit of the marshal arts. In the marshal arts particularly karate and the like, blows are intentionally directed to extremely vulnerable areas of the body and especially the groin. This intentional direction of such groin blows presents particular difficulties when training novices in the marshal arts and in competition. The objective in the training of students is to teach them to direct blows to specific points on the body while controlling the force of the blow so directed to eliminate injury to the opponent. However, due to the inexperience of the novice controlling of the force of the blow is not always accomplished and the opponent may be struck with a very forceful blow. When the blow is directed to and contacts the genitals and nearby areas, severe injury will be encountered. Although the opponent may wear a cup, the upward character of the blow obviates the protection provided by such cup.

In competition, experts in the marshal arts oppose one another and scoring is contingent on critical blows. A blow to the groin in an upward or angular direction is a high scoring blow. If such a blow is not sufficiently controlled, the receiver of such a blow can be severely injured.

In accordance with the present invention a protective device for the groin area is provided which effectively prevents injury due to both perpendicular, parallel and angular blows to the groin.

BRIEF DESCRIPTION OF THE INVENTION

A protective device is comprised of a rigid cup having sufficient volume to enclose the male genitals. A resilient padding is mounted on the edge of the cup and is adapted to contact the lower body. The resilient padding absorbs the impact experienced by the cup. The resilient padding on the cup edge engages the body proximate to the superior ramii, the inferior ramii and the Ischial ramii of the pelvis with minimal contact with the interior upper thighs. The protective device so constructed causes impact experienced by the cup to be absorbed by the padding and the aforementioned portions of the pelvis.

BRIEF DESCRIPTION OF THE DRAWINGS

FIG. 4 is a side view of a protective device of the invention partially in section;

FIG. 5 is a cross sectional view taken along the 5—5 line of FIG. 4; and,

FIG. 6 is a top view of a protective device of the invention partially in section.

DETAILED DESCRIPTION OF THE INVENTION

Figure 1:
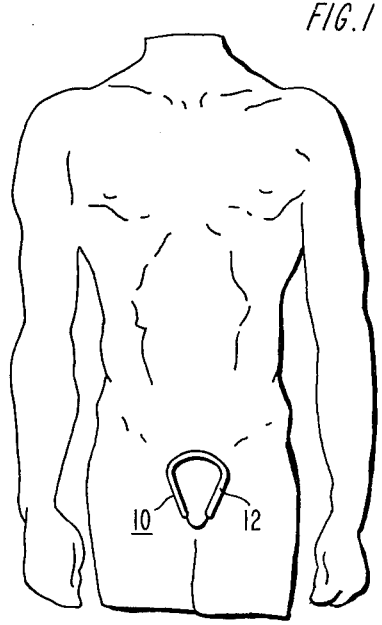
FIG. 1 is a front view of a protective device of the invention being worn by a man.
Figure 2:
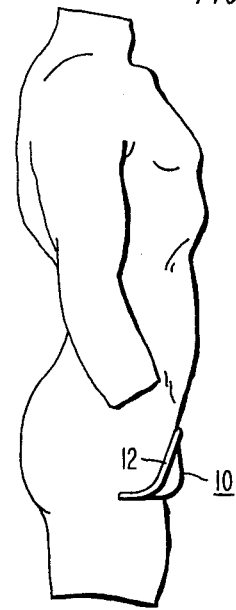
FIG. 2 is a side view of a protective device of the invention being worn by a man.
Figure 3:
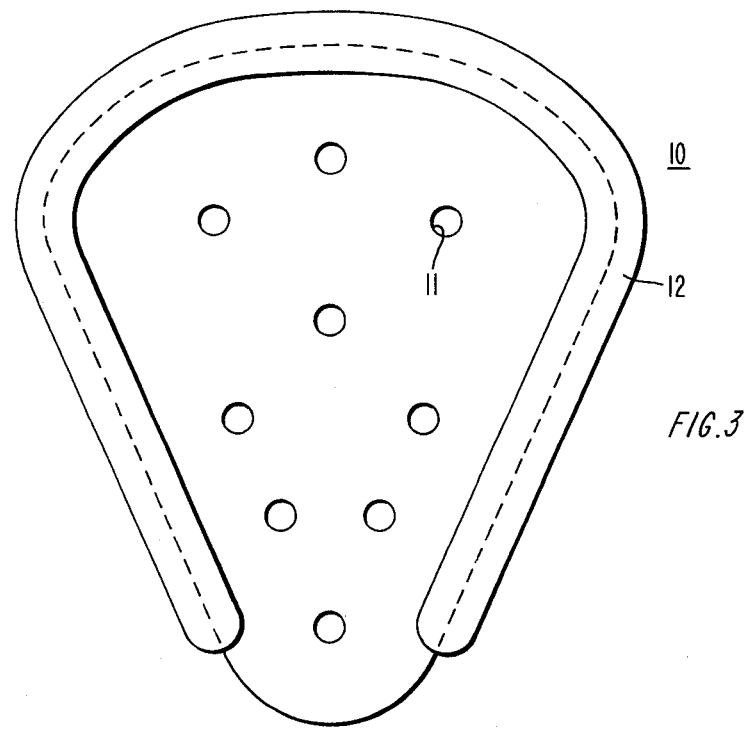
FIG. 3 is a front view of a protective device of the invention partially in section.

Referring now to the drawings in which like reference numerals refer to like parts in the various FIGURES, a cup 10 is constructed of a rigid plastic material. The plastic material of construction of the cup 10 is polypropylene, high density polyethylene or a similar material sufficiently rigid so that the cup retains its shape when impacted. Although virtually any rigid plastic material may be used in the construction of cup 10, care must be taken to insure that the plastic material is sufficiently inert and possesses non-irritating characteristics to prevent groin rashes. In one embodiment of the invention the cup 10 is extruded from Hercules GR1 extrusion grade polypropylene. The cup 10 may be extruded, vacuum formed, molded or formed by any suitable process.

A plurality of apertures 11 are provided in cup 10 to afford ventilation to the groin area. Although the apertures 11 are unnecessary as far as protecting the genitals and the area associated therewith, the ventilation makes the protective device more comfortable.

The $x$ portion of cup 10 has sufficient volume to contain the male genitals and the $y$ portion of cup 10 extends between the upper thighs.

Resilient padding 12 is mounted on the edge of cup 10 and is adapted to contact the lower body and absorb impact experienced by the cup 10. The resilient padding 12 is preferably foamed natural rubber, or flexible polyurethane foam. In one embodiment of the invention the resilient padding 12 is Craton Polyfoam flexible foam.

The resilient padding 12 is generally tubular having a slit 13 therein for mounting on the edge of cup 10. If desired the resilient padding 12 may be covered with a sheet of thin plastic 14 such as vinyl polyethylene or the like.

The resilient padding 12 is mounted on the edge of cup 10 to engage the pelvic area proximate to the superior ramii, the interior ramii and the Ischial ramii with minimal contact with the upper thighs. Thus, the resilient padding 12 absorbs some of the impact while the aforementioned portions of the lower pelvis absorb the remainder of the impact.

The $y$ portion of the cup 10 is elongated and narrowing rearwardly thus contouring to the interior of the upper thighs and allowing for freedom of movement.

Also the y portion of cup 10 protects the area proximate thereto and prevents the x portion of cup 10 from sliding up and injuring the genitals.

The protective device may be mounted to the body by straps or by means similar to that used in mounting the conventional cup. A waist band with a pouch capable of containing the protective device and buttock traversing bands is an effective means of mounting on the body.

Although the protective device is extremely useful in protecting the male groin during the practice of the marshal arts, it may be used for protection in other contact sports. In any event, the protective device of the invention provides greater protection than the conventional cup.

What is claimed is:

1. A protective device comprising:
    a rigid cup having sufficient volume to enclose the male genitals;
    resilient padding mounted on the edge of said cup said resilient padding adapted to contact the body at the lower portion thereof and absorb impact experienced by said cup;
    the resilient padding on the edge of said cup adapted to engage the body proximate to the superior ramii, the inferior ramii and the Ischial ramii of the pelvis with minimal contact with the upper thighs; and,
    wherein when an impact is experienced by said cup it is absorbed by the padding and the aforementioned portions of the pelvis.

2. The protective device of claim 1 wherein said cup has a plurality of apertures therein.

3. The protective device of claim 1 wherein said resilient padding is flexible foam.

4. A protective device comprising:
    a rigid cup having sufficient volume to enclose the male genitals;
    a rearwardly extending portion perpendicular to said cup and integral therewith;
    resilient padding along the edge of said cup and said rearwardly extending portion; and,
    said rearwardly extending portion having convergent edges.

5. The protective device of claim 4 having a plurality of apertures in said rigid cup.

6. The protective device of claim 4 wherein said resilient padding is flexible foam.

* * * * *